(12) United States Patent
Hodges

(10) Patent No.: US 6,669,094 B2
(45) Date of Patent: Dec. 30, 2003

(54) METHOD OF EMBEDDING AND RECOVERING ENCODED ITEM IDENTIFICATION INFORMATION IN AN EMULSION BY MEANS OF RADIANT ENERGY

(75) Inventor: Jan N. Hodges, 6078 Monterey Rd., Apt. #204, San Jose, CA (US) 95138

(73) Assignee: Jan N. Hodges, San Jose, CA (US)

(*) Notice: Subject to any disclaimer, the term of this patent is extended or adjusted under 35 U.S.C. 154(b) by 75 days.

(21) Appl. No.: 10/067,032

(22) Filed: Feb. 4, 2002

(65) Prior Publication Data

US 2003/0146281 A1 Aug. 7, 2003

(51) Int. Cl.⁷ .......................... G06K 7/00; G06K 19/06
(52) U.S. Cl. ..................................... 235/486; 236/492
(58) Field of Search ................... 235/487, 492, 235/494, 493, 375, 441, 380, 381, 382.5, 486

(56) References Cited

U.S. PATENT DOCUMENTS 4,863,819 A * 9/1989 Drexler et al. ............... 430/14
4,937,810 A * 6/1990 Drexler et al. ............ 369/275.1
5,340,968 A * 8/1994 Watanabe et al. ........... 235/380
5,992,743 A * 11/1999 Suemoto et al. ........ 235/462.05
6,283,375 B1 * 9/2001 Wilz et al. .............. 235/462.45
6,491,215 B1 * 12/2002 Irwin et al. ................ 235/375

* cited by examiner

Primary Examiner—Thien M. Le (57) ABSTRACT

This process and apparatus induces an artificial quantity of a number of sequentially tuned discreet frequencies, in specific bandwidths and timeframes, into an encoded composition target of a number of receptive elemental resonators, not present in natural formations, which respond in kind, with programmed user formulation, by emitting combinations of intelligent pulses at corresponding specific frequencies and time periods. These pulses are detected, from the medium, and are converted to registered combinations of data that are associated with the target identification, providing a better, more comprehensive and cost effective means for the encoding and decoding of individual item identification data, without the use of existing passive identification methods, for collection and management, within existing Supply Chain and Asset Management tracking infrastructures.

3 Claims, 8 Drawing Sheets

| Symbol | Element Name | Weight | Frequency | | Wavelength | | Photon λ | |
|---|---|---|---|---|---|---|---|---|
| Pt | Platinum | 195.09 | 58.48642128 | EHz | 0.005125847 | nm | .22479 | nm |
| Au | Gold | 196.97 | 59.05003024 | EHz | 0.005076923 | nm | .22408 | nm |
| Pd | Palladium | 106.4 | 31.8978688 | EHz | 0.009398511 | nm | .20788 | nm |
| Li | Lithium | 6.939 | 2.080256688 | EHz | 0.144113205 | nm | .20788 | nm |
| Ag | Silver | 108.7 | 32.5873904 | EHz | 0.009199646 | nm | .20786 | nm |
| Be | Beryllium | 9.0122 | 2.701785462 | EHz | 0.110960867 | nm | .20249 | nm |
| V | Vanadium | 50.94 | 15.27140448 | EHz | 0.019630968 | nm | .19905 | nm |
| Mn | Manganese | 54.93805 | 16.46998789 | EHz | 0.018202348 | nm | .19750 | nm |
| Cu | Copper | 63.54 | 19.04878368 | EHz | 0.015738142 | nm | .19691 | nm |
| Co | Cobalt | 58.9332 | 17.66770189 | EHz | 0.01696839 | nm | .19617 | nm |
| Ti | Titanium | 47.9 | 14.3600368 | EHz | 0.020876859 | nm | .19568 | nm |
| Kr | Potassium | 39.102 | 11.72246678 | EHz | 0.025574179 | nm | .19523 | nm |
| Cr | Chromium | 51.996 | 15.58798483 | EHz | 0.019232278 | nm | .19471 | nm |
| B | Boron | 10.811 | 3.241051312 | EHz | 0.092498523 | nm | .19432 | nm |
| Fe | Iron | 55.85 | 16.7433832 | EHz | 0.01790513 | nm | .19305 | nm |
| Sc | Scandium | 44.956 | 13.47744915 | EHz | 0.022244006 | nm | .19240 | nm |
| Ni | Nickel | 58.693 | 17.59569186 | EHz | 0.017037833 | nm | .18839 | nm |
| Na | Sodium | 22.9898 | 6.892158122 | EHz | 0.043497618 | nm | .18783 | nm |
| Cl | Chlorine | 35.453 | 10.62852578 | EHz | 0.028206401 | nm | .18743 | nm |
| Al | Aluminum | 26.9815 | 8.088837848 | EHz | 0.037062488 | nm | .18653 | nm |
| P | Phosphorus | 30.984 | 9.288755328 | EHz | 0.032274772 | nm | .18564 | nm |
| Mg | Magnesium | 24.312 | 7.288543104 | EHz | 0.041132014 | nm | .18208 | nm |
| Si | Silicon | 28.086 | 8.419958112 | EHz | 0.035604982 | nm | .18030 | nm |
| Ca | Calcium | 40.08 | 12.01566336 | EHz | 0.024950138 | nm | .18010 | nm |
| S | Sulfur | 32.064 | 9.612530688 | EHz | 0.031187672 | nm | .18010 | nm |
| C | Carbon | 12.0112 | 3.60086167 | EHz | 0.083255755 | nm | .17991 | nm |
| He | Helium | 4.0026 | 1.199947459 | EHz | 0.249837987 | nm | .17986 | nm |
| H | Hydrogen | 1.00797 | 0.302181342 | EHz | 0.992094535 | nm | .09059 | nm |

Fig. 5

| Lower Visible Light | | 428 | Thz | 700.4496685 | nm |
|---|---|---|---|---|---|
| Far Infrared | | 299.792 | Thz | 1.000001528 | μm |
| Yag Laser | | 282.823 | Thz | 1.060000276 | μm |
| Infared Radiation | | 29.979 | Thz | 10.00008199 | μm |
| Highest MircoWave | | 11.992 | Thz | 24.99937109 | μm |
| Near Infrared | | 2997.92 | Ghz | 100.0001528 | μm |
| Hydrogen Line | | 2110.6 | Ghz | 142.0413428 | μm |
| EHF | | 299.795 | Ghz | 999.9915212 | μm |
| Bose | | 214 | Ghz | 1.400899337 | mm |
| 802.11 | | 2.4 | GHz | 124.9135242 | mm |
| SHF | | 29979.25 | Mhz | 0.009999999 | m |
| UHF | | 2997.925 | Mhz | 0.099999986 | m |
| VHF | | 299.792 | Mhz | 1.000001528 | m |
| Microwave | | 13.56 | Mhz | 221.0858836 | m |
| HF | | 2997924.6 | Hz | 99.99999937 | m |
| Lower Infrared | | 428000 | Hz | 700.4496685 | m |

METHOD OF EMBEDDING AND RECOVERING ENCODED ITEM IDENTIFICATION INFORMATION IN AN EMULSION BY MEANS OF RADIANT ENERGY

FIELD OF THE INVENTION

The present invention relates generally to the field of INVISIBLE RADIANT ENERGY RESPONSIVE ELECTRIC SIGNALING. This process and apparatus induces an artificial quantity of sequentially tuned frequencies, in and above, the Near Infrared bandwidth, at specific time frames, into an encoded composition target of receptive elemental resonators, not present in natural formations, which respond in kind, with programmed user formulation, by emitting combinations of intelligent pulses. These pulses are received, by a Collector, and converted to data, specifying the target signature and/or identification.

BACKGROUND

The need to identify an item forms the roots of all languages and enables societies to formulate growth and stability, based on this information. However, the multitude of languages and the various designations, of a specific item, had often created difficulties in cross-linguistic exchanges.

In commerce, a common language of numerical indicators was applied, leading to UPC bar-coding methods and improved methods of categorization for every item on earth. Managing these categories has become a significant task. Supply Chain Management has become a substantial industry, focusing on the simple question, "Where is that item?" The latest entry, into the solution suite of techniques used to identify and track items, is Radio Frequency Identification (RFID). Through the use of a microchip, placed upon an item, a radio transponder is able to 'read' the digital information, programmed into the chip that identifies the host item and relay this information back to an infrastructure of data correlation and reporting. Vast, worldwide infrastructures have been created to 'track' these RFID tags. The use of RFID to track Conveyance (container) devices has proven to be the most beneficial, technical and economically sound application to date.

The major drawback to current RFID tagging technology: The Conveyance may arrive, but the individual items, contained within, may not. RFID microchips are unable to be produced economically low enough, and are unable to overcome limitations in the upper bandwidths of the electromagnetic spectrum, to be applied at the 'item level'.

This invention addresses the need for an 'item level' identification medium, that will be able to interface with existing supply chain infrastructures and provide the next level in item identification technology.

To begin the explanation of how this invention (SMEAR) functions, an overview of why it is possible, should be presented.

A photon is an elementary particle, traveling at the speed of light. In itself, it does not carry energy and energy properties cannot be assigned to it, either in a single photon or a wave. The exchange rate, of the photon's less potential energy perimeter, inward to the highest potential energy concentration, produces resonant properties at a specific rate or frequency, identifying the particle properties. Imparted energy output, equated to each particle, is a result of an encounter with a mass of dissimilar (from the particle) constituent particles, resonating at a state of dynamic equilibrium.

During, and resulting from, the dissimilar particle encounter, hereunder known as a Photon Event (FIG. 2), each particle exchange has an energy output of 2 eV during the $10E^{-27}$ second event (202), thus producing 'noise', in a number of beat and superposition bandwidths.

This is the period at which Light properties are exhibited and energy outputs are registered.

For categorizing, the base frequency of a single photon, determines the model and properties of the element, to which the photon is associated (FIG. 4).

Presently, there are two ways to detect these residual photon emissions in the lower wavelengths; a) through radio-reception techniques, in a bandwidth from 30 MHz to 1 Thz. (Present day heterodyne receivers, used in the upper frequencies, are pushing the quantum limit of the superconductor-insulator-superconductor (SIS) material used in the receivers at 700 GHz). And b) Optically, by use of conventional telescopes and image enhancement systems and spectrometry techniques, to graphically interpret the frequencies of photons, providing specific signatures to their origins. However, with these present day radio and spectroscopic technologies, limits have been reached in the application of these particles.

Figure 5:
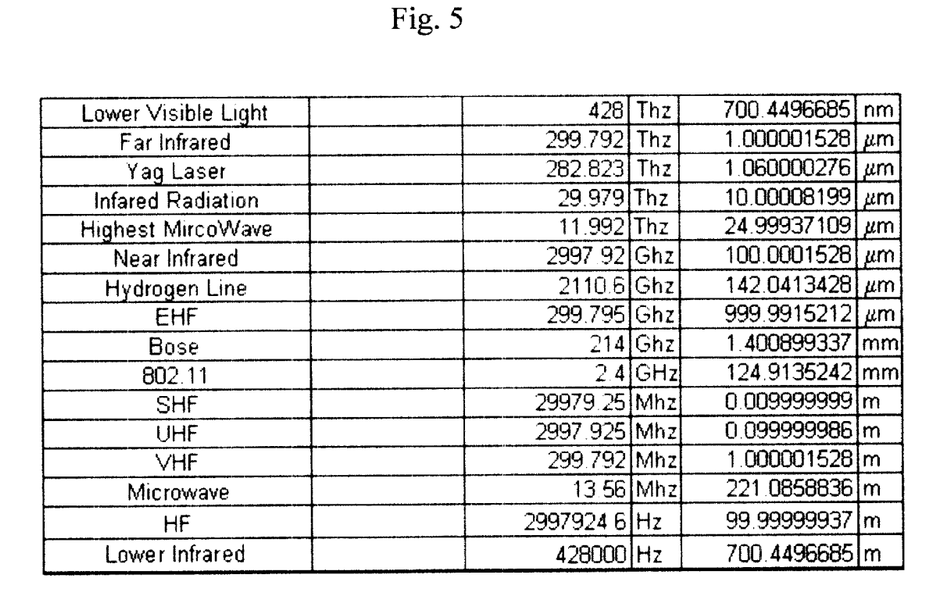
FIG. 5 is a chart indicating bandwidth of SMEAR.
Figure 6:
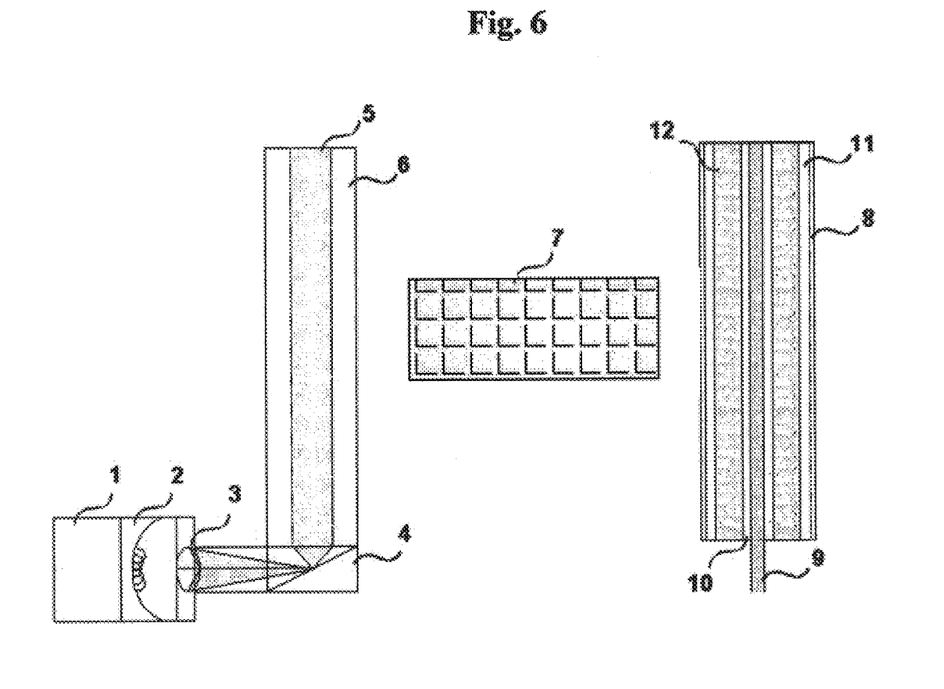
FIG. 6 is a graphic description of a standard SMEAR system.
Figure 7:
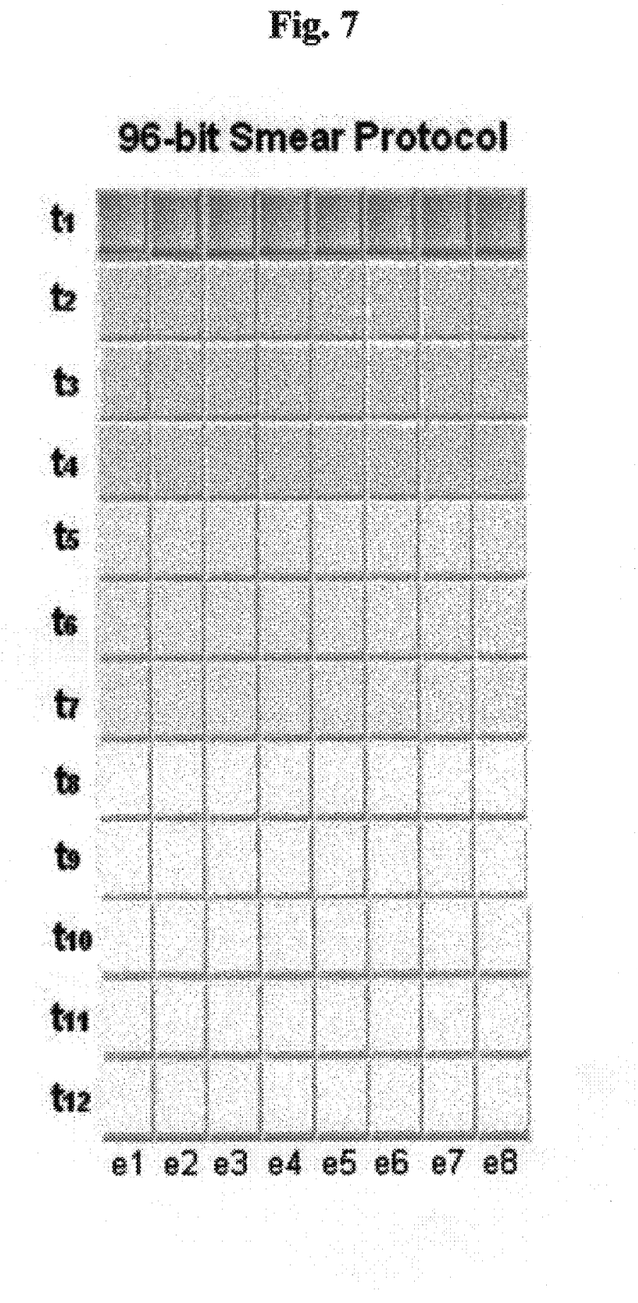
FIG. 7 is a matrix, indicating a 96-bit Protocol utilized by the Smear system.

The inspiration, behind this invention, was to utilize existing infrastructures of data collection processes and incorporate quantum mechanisms into the area of 'item-level' data detection and collection, through the down-conversion of the above mentioned photon event properties, originating above the 700 nm bandwidth, and resonating downward, to the Near Infrared (1 $\mu$m–100 $\mu$m) bandwidth of the electromagnetic spectrum (FIG. 5).

SUMMARY OF THE INVENTION

The present invention is directed to a method of embedding and recovering encoded item identification information in a multi-element emulsion (Smear) which comprises (a) item specific data in a predetermined item identification code format, in a substrate, with a polymer marking material having multiple states corresponding to a specific series of absorption spectrums, changing to multiple second states corresponding to a specific series of emitted frequency spectrums; and (b) thereafter effecting multiple specific reactive frequency changes of the encoded polymer marking material from the first state to multiple second states (c) producing binary data radiant emissions which can be detected in the Near Infrared, and above, bandwidth and associated to individual items.

BRIEF DESCRIPTION OF THE DRAWINGS

The present invention is illustrated by way of example in the following drawings in which like references indicate similar elements. The following drawings disclose various embodiments of the present invention for purposes of illustration only and are not intended to limit the scope of the invention.

FIG. 4 displays the Elementary Particle frequency chart, indicating base frequency emissions used in calculating SMEAR signatures.

DETAILED DESCRIPTION

Figure 2:
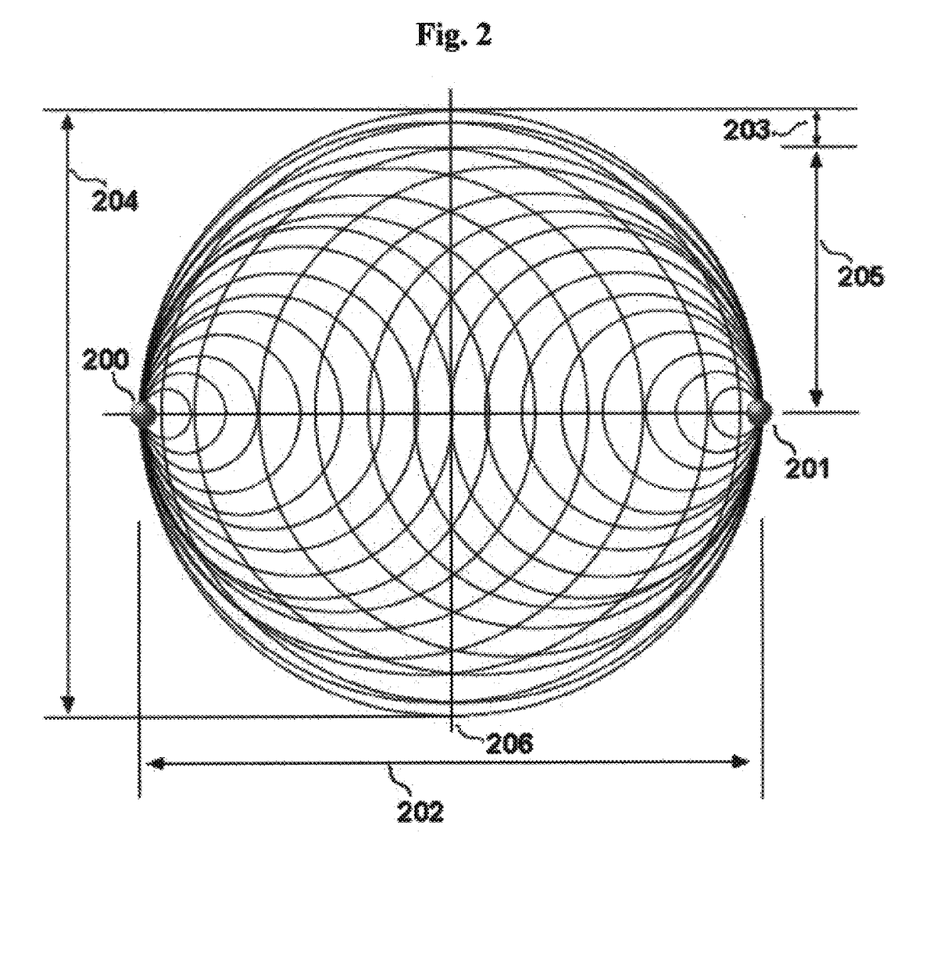
FIG. 2 is a depiction of occurrences during a Photon Event.
Figure 3:
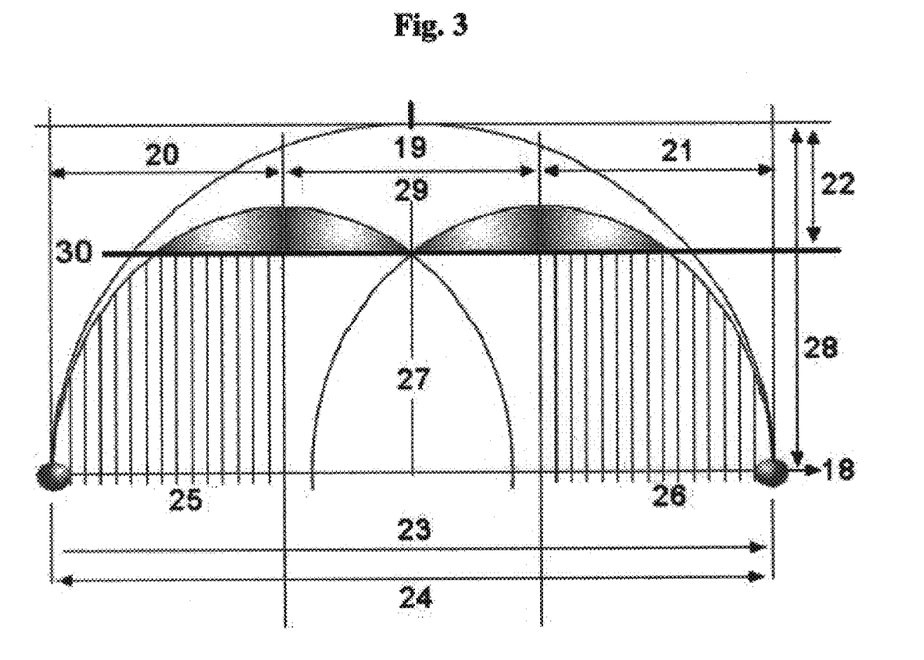
FIG. 3 is a graphic representation of Particle Classification.

An Elementary Particle is 'static' as long as its' specific oscillations, inward from all directions, are synchronized and undisturbed by outside influences. When a particle encounters a mass, of a dissimilar frequency as shown in FIG. 2, the resultant cross-modulation frequencies will induce perpendicular field effects on the spherical boundaries of the particle, from the point of mutual contact (200). The Particle field diction will dissipate the energy bundle to a point of near absolution, absorbing any surrounding weaker fields. Upon reaching a mass that exhibits a stronger negative shell, to the positive core, the field will reform to electrical normalcy (201).

This absorption/emission affect, hereunder a Photon Event, may affect up to 100,000 dissimilar particles, within the encountered mass' outer layer (204) in the localized area of $2.817^{-15}$ CM.

This effect, the result of the combined interference of the two dissimilar frequencies, will appear to slow down the external frequency 'field' in respect to the Particles' radial wavelength expansion. (As the wavelength increases, the frequency decreases to a longer time frame of existence) (205). This slower 'encompassing frequency field' exhibits wave properties, from the negative (less positive potential) peripheral of the Particle oscillations—to the concentrated, more positive potential, internal core.

This lowered frequency effect will result in an expansion of the affected Particles' spherical boundaries (204), each 'growing' to the size of an electron ($10^{-15}$ cm), thus enabling the Particle, at equilibrium apogee (zero point between absorption and emission) (206) to disrupt the properties of a near-field electron.

As the energy imparted shell reaches the equilibrium apogee (19, 206), the peripheral resonance will pass into (shift) and below visible light (203). This event, from absorption to emission, occurs within $10^{-27}$ of a second (202, 24).

The photo ionization rates depend linearly on the excitation intensity and the incident frequency (30), indicating that the ionization process occurs via a single photon.

A Photon Event occurs when dissimilar electromagnetic radiation frequencies encounter an Elementary Particle (FIG. 2). Most of the radiation continues in its original direction, until absorbed into stronger potentials, but a small fraction is scattered in other directions. This scattering of spontaneous emissions, occurring from a coherent excited SMEAR population, is defined as Raman scattering.

Figure 1:
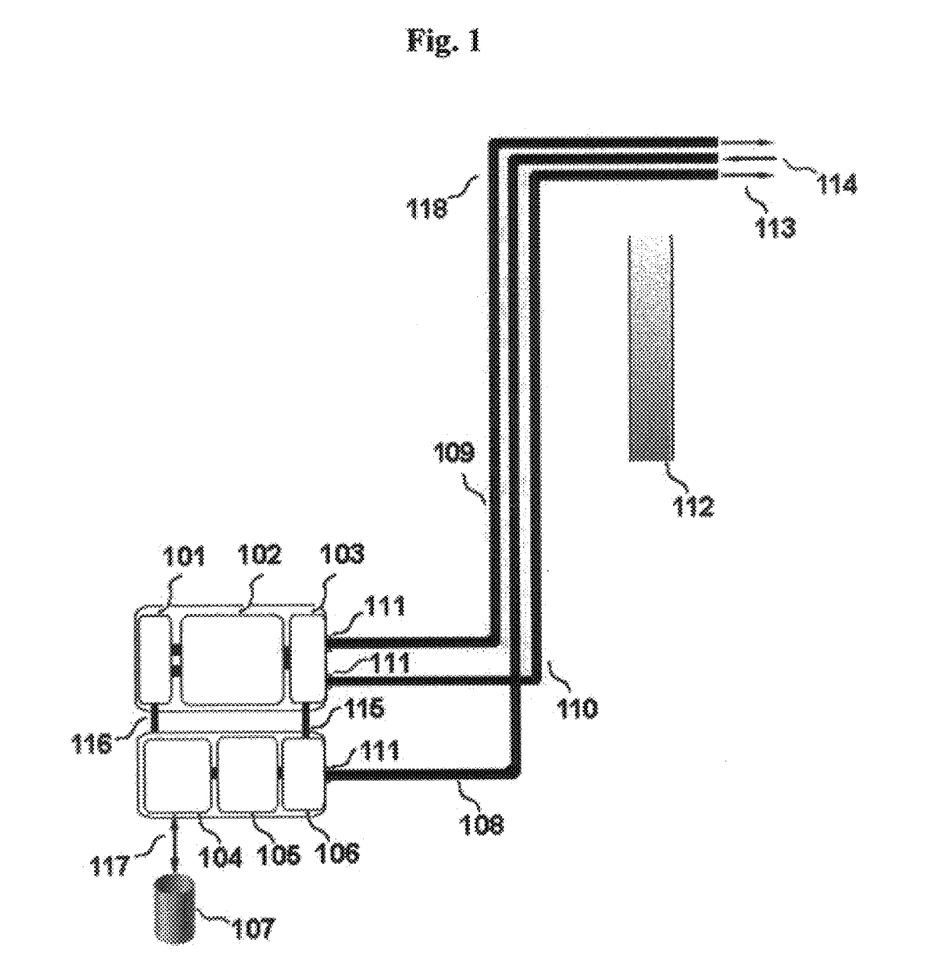
FIG. 1 is a graphic representation of the Smear apparatus.

Radiant frequencies that are scattered, due to vibrations in elementary particles, are called Raman Scattering. Raman scattered SMEAR frequencies are shifted (22), by as much as, 4000 cm$^{-1}$, from the incident sequence frequencies (102) of the Striker.

The elementary particle frequency signature emissions, from the coherent SMEAR population, will be resonantly enhanced, while the incoherent population will cause normal fluorescence. Also, there will be losses from the excited state population, due to non-radiative relaxation. All of these losses result in absorption of light frequencies.

The ratio of fluorescence to Ram an will be approximately 2/(T2*GAMMA) where T2 is the dephasing time constant and GAMMA is the radiative rate of spontaneous emission.

The emitted frequency (22) will differ from the exciting frequency (30) by the energy of the final state, per the effected elementary particle's frequency (FIG. 4). This signature is collected in phased-locked events (115), from Striker to Collector, and read in binary sequence, as shown in a 96-bit protocol in FIG. 9. (Where t1–t12 are twelve Striker incident frequencies, in twelve sequential time-frames, and e1–e8 are eight Elements (FIG. 4) incorporated into the Smear emulsion.)

To an Observer, viewing a single photon event in visible light and in 'real time', this action appears as a 'blinking off and on' or sparkle. With a continued flow of photons, as illumination from a constant radiation source (sun, lamp, fire), the continuous photon events provide reflective recognition of any object the photons are contacting.

During a photon event, a single particle will absorb and reach the diameter of an electron (0.29 nanometer) and exhibit electron properties in a superposition bandwidth. It will then return to its original size (emission), imparting energy (spurious sweeping emission frequencies) in the vortex, exhibiting negatively charged properties.

When a single photon, contacts a mass, of a dissimilar frequency composition, the interaction results in disruption, both, in superposition and beat. The resultant vibration is given in a combination that lends itself to attraction from a higher frequency particle, resulting in the eventually formation of Atoms, then Molecules.

The resultant Beat frequency modulation, of the two dissimilar particles' encounter; will produce resonance within the lower bandwidths of the Electromagnetic Spectrum (205, 203).

This resultant resonance can be converted to intelligent energy, as It beats and interferes with frequencies within this electromagnetic level of the frequency spectrum.

This invention utilizes the resultant beat frequency, cross-modulation, of dissimilar photon interactions, as they manifest within, and above, the Near Infrared bandwidth. Infrared frequencies are positioned within the portion of the electromagnetic spectrum (203), just below the visible light range (FIG. 5). This bandwidth is detectable between 2997.92 GHz and 299.792 THz, or 100 $\mu$m–1 $\mu$m.

This is not selective reflection, for the wavelength emissions do not correspond with those of the absorption bands of the suspension media, i.e. ink, paint, glazes. Nor is it selective radiation, being relative to spectral energy distribution in the form of color temperature.

This process and apparatus induces an artificial quantity of sequentially tuned frequencies into a composition of receptive resonators, not present in natural formations, which respond in kind, with programmed accuracy, by emitting combinations of intelligent pulses at specific frequencies, within and above, the Near Infrared bandwidth.

SMEAR is the designation for an emulsion, which is composed of coded particulate nodules, suspended in a substrate, where each nodule carries a 'signature' or code identified by the intensity and wavelength response, to a number of specific 'encounters' with dissimilar particles in controlled time frames.

The present invention is directed to a process for embedding and recovering coded item identification information on an object. More specifically, the present invention is directed to a process for embedding encoded item identification information, which can, by irradiation with radiation of appropriate sweeping wavelengths, within and above the Near Infrared bandwidths, be resonated to radiant transmittal, received and associated with specific items or products.

One embodiment of the present invention is directed to a method of embedding and recovering encoded item identification information in a multi-element emulsion (Smear) which comprises (a) item specific data in a predetermined item identification code format in an ink substrate with a polymer marking material having multiple states corresponding to a specific series of absorption spectrums, changing to multiple second states corresponding to a specific series of emitted frequency spectrums; and (b) thereafter effecting multiple specific reactive frequency changes of the encoded polymer marking material from the first state to multiple second states (c) producing binary data radiant emissions which can be detected in the Near Infrared, and above, bandwidths and associated to individual items.

Figure 8:
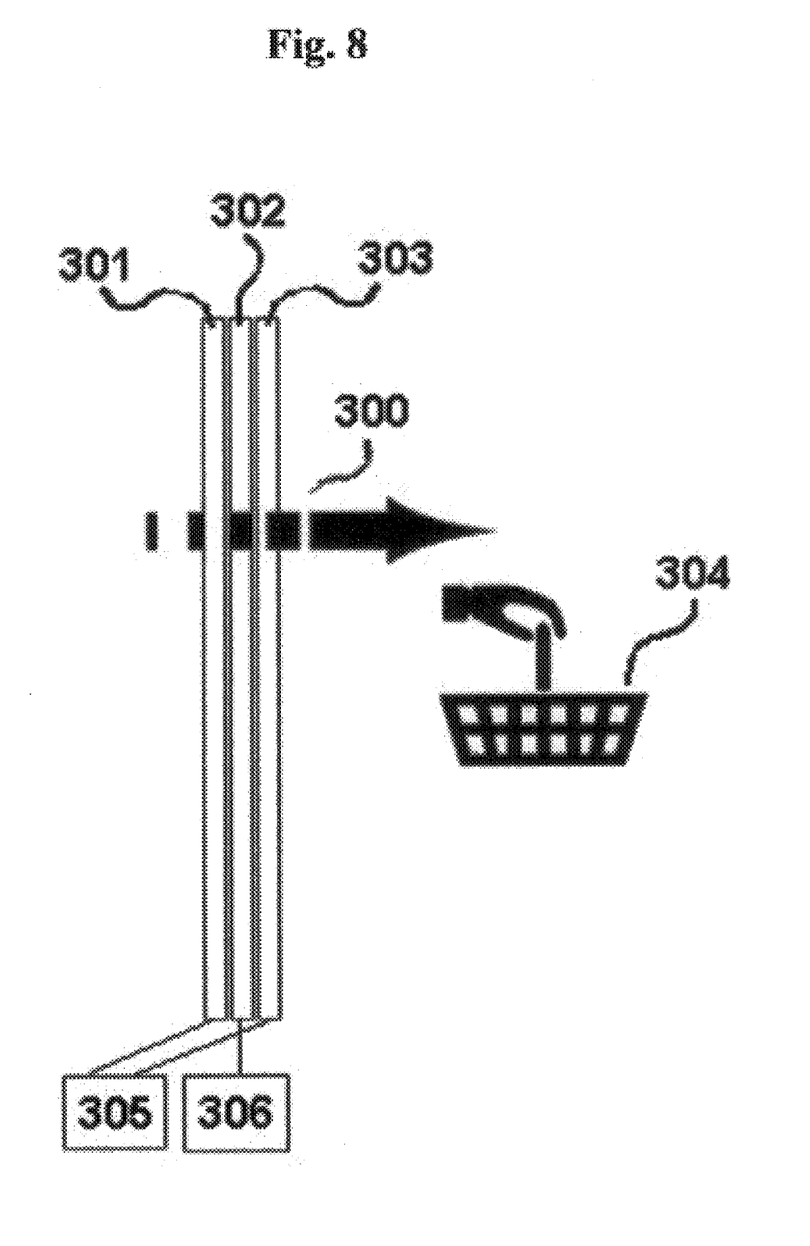
FIG. 8 is a graphic illustration one embodiment of the invention, at a Choke Point.

An enclosure (305), physically located at a chosen point of concentrated item activity (Choke Point) (300), where Smear emulsion data is to be collected, contains a Power Supply (101), the Signal Generator (102), the Emitter Array assembly (103) and connection points (111) for the two Striker antennae (109, 110, 301, 303).

Located, at the same physical location of the first enclosure, and sharing the same power supply (101, 116), is an additional enclosure (306) which contains a connection (111) for attaching the Collector antenna (108, 302), a Converter (106) for converting the electrical signals outputted from said Collector picking-up means into binary data, a Stochastic Adaptor (105) for analyzing the binary data derived from said binarizing means and a Data Center (104) for association, storage and retrieval of the resultant decoded identification of the encoded emulsion (112). An External Data Center (107) may also be employed, by means of a remote connection (117).

Collector and Striker are phase modulated for synchronicity (115).

The Striker and Collector antennae are fiber optic, in nature, and are capable of following the physical contours of Choke Points (118, 300).

Further methods for incorporating SMEAR compounds into a carrier composition may be by coating or encapsulating such compounds in a polymer shell in the form of microcapsules.

Coated SMEAR compounds may be formed by coating the finely divided SMEAR compounds with a solution of a polymer, in a volatile solvent, and then rapidly evaporating the solvent. The microencapsulated SMEAR compounds are prepared according to well-known methods of microencapsulating or coacervation using gelatin or acacia gum as a wall material or by encapsulation of the SMEAR compound together with water-insoluble polyamines and water-soluble bisulfite adducts of polyisocyanates as described for example in U.S. Pat. Nos. 4,428,978 and 4,517,141, which are incorporated herein by reference. other methods for incorporating the SMEAR compounds into a polymer are by imbibition, into the particles of the polymer or by extruding, molding or casting with the polymer. For polymers that are used as protective overlays, the SMEAR compounds may be added to the adhesive used to attach the overlay, taking into consideration the concerns cited hereinafter for directly incorporating the SMEAR compounds.

The SMEAR compounds can be added to clear inks and coatings, resulting in solutions of approximately 1% concentration on a weight basis.

Sequential radiation of the emulsion will provide discrete emissions, resulting in a cascade of data relating to each absorption/emission elemental property of the Smear.

What is claimed is:

1. A process for embedding and retrieving identification information, in an emulsion, affixed to and designating individual Items, by use of Radiant Energy identification methods:

The steps and apparatus comprising:
A. a Near Infrared, and above, swept-wavelength generator (102); Signal Generator
B. an optical antenna (109, 110) capable of emitting multi-frequencies (113), within and above, the Near Infrared bandwidth; Striker
C. an encoded emulsion (112); Smear
D. an optical antenna (108) capable of receiving multi-frequencies (114), within and above, the Near Infrared bandwidth; Collector
E. a binarizing means for converting the electrical signals outputted from said Collector picking-up means into binary data (106); Converter
F. an analyzing means for analyzing the binary data derived from said binarizing means and reading SMEAR information (105); Stochastic Adaptor
G. a Data Center (104, 107) for association, storage and retrieval of the resultant decoded identification of the encoded emulsion.

2. A method according to claim 1 wherein the resultant resonance changes, in the emulsion coded material, from the first state to multiple second states is effected by irradiation with radiation at a specific series of selected wavelengths, and time periods, within and above the Near Infrared bandwidth.

3. A process and apparatus according to claim 2 wherein said method is implemented for non-intrusive, frequency-sensitive identification material technology within item tracking infrastructures:

a. The signal generator (102), and associated power supply (101), apparatus of claim 1 wherein said Frequency Generator is a swept multi-frequency source, within and above, the Near Infrared bandwidth of 2997.92 GHz–299.792 THz (100 μm to 1 μm) (FIG. 5), facilitated by a multi-wavelength-specific frequency emitter array (103);

b. The signal generator of claim 1 wherein said Frequency Generator is coupled (111) to quartz optical fibers (109, 110), bundled in a flexible (118) optical antenna array of said Striker;

c. The resonator apparatus of claim 1 wherein said Striker emits the Signal Generator output (113), rapidly progressing through a sequential series of selected wavelengths, within and above, the Near Infrared bandwidth, and cross-modulates frequency sensitive particles, within the SMEAR target (112);

d. The SMEAR emulsion is composed of coded particulate nodules, 1 to 40 nm in diameter, suspended in a substrate, where each nodule carries a 'signature' or code consisting of intensity and wavelength scatter—this identifies each nodule. The multi-bit programmable signature (XXX) of the emulsion formula, resonated at a specific series of particle scatter wavelength(s), can facilitate a trillion-trillion 'signature' data mixtures. The SMEAR composition is chemically compatible with a variety of ink, paint and ceramic coating compounds. Being uniformly dispersed or dissolved within a matrix for producing ionic resonant reactions in response to a series of specific radiation wavelengths striking the coded imprint;

e. The detector apparatus of claim 1 wherein said Collector (108) is a device sensitive to frequencies, within and above, the Near Infrared bandwidth. The flexible (118) Collector receives (114) sequential data packets of a target's imprint; characterized in that the Collector is designed in order to detect resultant data packets of emitted frequencies, from said radiated source target Smear (112), which is directly resonated and singularly scattered from the target imprint, at specific cross-modulated frequencies;

f. The antennae apparatus of claim 1 wherein said Striker and said Collector are phase modulated in synchronicity (115);

g. The resonator apparatus of claim 1, known as the Striker, wherein said frequency generator supplies specific discreet wavelengths and said Collector is connected (111) to a Converter (106) for processing the electrical signals outputted from said Collector picking-up means into binary data;

h. Firmware and processing circuitry, wherein said Stochastic Adaptor (105), provides means for analyzing the binary data derived from said Converter;

i. Smear Emulsion data is stored within an internal (104) or external (107) Data Center for management.

\* \* \* \* \*